United States Patent [19]

Hashimoto et al.

[11] 4,192,958
[45] Mar. 11, 1980

[54] METHOD FOR RECOVERING RESORCINOL

[75] Inventors: Isao Hashimoto, Waki; Hiroaki Nakagawa, Iwakuni; Hirohiko Nambu, Ohtake, all of Japan

[73] Assignee: Mitsui Petrochemical Industries Ltd., Tokyo, Japan

[21] Appl. No.: 945,883

[22] Filed: Sep. 26, 1978

[30] Foreign Application Priority Data

Sep. 30, 1977 [JP] Japan ................... 52/116887

[51] Int. Cl.$^2$ ............................. C07C 39/10
[52] U.S. Cl. ................................. 568/763
[58] Field of Search ............. 568/753, 754, 763, 768

[56] References Cited

U.S. PATENT DOCUMENTS 2,728,793  12/1955  Armstrong et al. .............. 568/754
3,180,897  4/1965   Sodomann et al. ............. 568/754

FOREIGN PATENT DOCUMENTS 739907  11/1955  United Kingdom ............ 568/754
775813  5/1957   United Kingdom ............ 568/754
982514  2/1965   United Kingdom ............ 568/754

*Primary Examiner*—Werren B. Lone
*Attorney, Agent, or Firm*—Sherman & Shalloway

[57] ABSTRACT

A method for recovering resorcinol by thermally cracking high-boiling by-products contained in the acid-cleavage product of m-diisopropylbenzene dihydroperoxide, wherein the thermal cracking is effected in the presence of an aromatic ketone of the formula

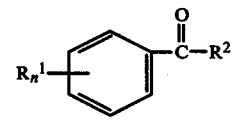

wherein $R^1$ represents a member selected from the group consisting of hydrogen, saturated alkyl groups having 1 to 6 carbon atoms, hydroxyl, acetyl and chlorine, $R^2$ represents a member selected from the group consisting of saturated alkyl groups having 1 to 6 carbon atoms, cyclohexyl and phenyl, and n represents 1, 2 or 3, and when there are two or more $R^1$ groups, they are identical or different.

4 Claims, No Drawings

METHOD FOR RECOVERING RESORCINOL

This invention relates to an improved method for recovering additional amounts of resorcinol by thermally cracking high-boiling by-products contained in the acid-cleavage product of m-diisopropylbenzene dihydroperoxide.

More specifically, the invention relates to a method for recovering additional amounts of resorcinol by thermally cracking high-boiling by-products contained in the acid-cleavage product of m-diisopropylbenzene dihydroperoxide, characterized in that the thermal cracking is effected in the presence of an aromatic ketone of the formula

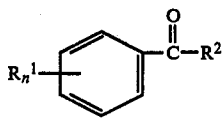

wherein $R^1$ represents a member selected from the group consisting of hydrogen, saturated alkyl groups having 1 to 6 carbon atoms, hydroxyl, acetyl and chlorine, $R^2$ represents a member selected from the group consisting of saturated alkyl groups having 1 to 6 carbon atoms, cyclohexyl and phenyl, and n represents 1, 2 or 3, and when there are two or more $R^1$ groups, they are identical or different.

Methods are known to produce resorcinol by acid cleavage of m-diisopropylbenzene dihydroperoxide (to be sometimes referred to as m-DHP) obtained by the oxidation of m-diisopropylbenzene (to be sometimes referred to as m-DIPB). The acid cleavage product is known to contain high-boiling by-products (by-products having a higher boiling point than resorcinol) in addition to resorcinol and acetone. It is assumed that these high-boiling by-products consist predominantly of a condensate between resorcinol and acetone, and condensates between resorcinol and olefins such as m-isopropenyl phenol.

It is commercially advantageous therefore to recover additional amounts of resorcinol by thermally cracking these high-boiling by-products, and methods of recovery have been suggested.

For example, British Pat. No. 739,907 discloses the recovery of additional amounts of resorcinol and m-isopropenylphenol from acid-cleavage by-products having a lower volatility than resorcinol (i.e., high-boiling by-products) by thermal cracking. British Pat. No. 775,813 discloses that the thermal cracking in the process disclosed in British Pat. No. 739,907 is carried out while passing an inert gas such as steam, nitrogen or carbon dioxide. Furthermore, British Pat. No. 982,514 discloses the process for the recovery of resorcinol from the product of the acid cleavage of m-diisopropylbenzene dihydroperoxide, which comprises distilling the cleavage product to remove low-boiling materials, heating the cleavage product substantially free from low-boiling materials but containing the resorcinol to vaporize substantially all of the products other than the high-boiling condensation products, cracking the residual liquid mixture under reduced pressure and with the aid of steam stripping to vaporize further quantities of resorcinol, condensing the combined products of the vaporizer and the cracking process, and recovering resorcinol therefrom.

In these prior techniques, cracking is performed while distilling off resorcinol in order to prevent recondensation of resorcinol formed by cracking. When the cracking proceeds and the thermally crackable ingredient decreases, the reaction mixture gradually becomes viscous and decreases in flowability. Consequently, the heat for reaction cannot be supplied smoothly by external heating. This not only causes a trouble to the cracking reaction, but also a tarry solid adheres to reactor walls, making it impossible to continue the reaction for long periods of time. British Pat. No. 739,907 states that to avoid such troubles, the cracking is carried out in the presence of a high-boiling substance which is substantially inert to resorcinol. It describes tri-isopropylbenzene, methylnaphthalene, isopropylnaphthalene, chloronaphthalene, bromonaphthalene and 1,2,4-trichlorobenzene as examples of the inert high-boiling substance. However, since the tarry solid is not soluble in such an inert high-boiling substance, it is virtually difficult to satisfactorily prevent the deposition of insoluble solids within the reactor or the adhesion of the solids to the reactor walls.

The present inventors made investigations in order to provide an improved method for thermally cracking high-boiling by-products contained in the acid-cleavage product, which can effect the cracking reaction efficiently, maintain the reaction mixture within the cracking reactor in a favorable flowing condition, and inhibit an undesirable coking phenomenon which causes, for example, the deposition of insoluble solids or the adhesion of solids by commercially advantageous means. These investigations led to the discovery that the aforesaid defects of the prior art can be advantageously overcome by performing the thermal cracking of the high-boiling by-products in the presence of the aromatic ketone of formula (1) given hereinabove, preferably m-hydroxyacetophenone, p-hydroxyacetophenone or a mixture of these.

It is an object of this invention therefore to provide an improved method for recovering resorcinol by thermally cracking high-boiling by-products contained in the acid-cleavage product of m-diisopropylbenzene dihydroperoxide.

The above and other objects and advantages of the invention will become more apparent from the following description.

It is known to produce m-DHP by air oxidizing m-DIPB and/or m-diisopropylbenzene monohydroperoxide in the liquid phase, and the reaction conditions used for this process are also well known. It is of course known that the resulting oxidation product containing m-DHP, either as such or after separating m-DHP from it, is subjected to acid cleavage to form resorcinol and acetone as main products, and high-boiling by-products are formed during the acid-cleavage.

For example, m-DHP, or the product of oxidation of m-DIPB containing m-DHP is sent to an acid-cleavage reactor together with a suitable acid-cleavage solvent, for example a ketone such as acetone, methyl ethyl ketone or methyl isobutyl ketone, or a hydrocarbon such as benzene, toluene, xylene or ethylbenzene. When the oxidation reaction product is directly used, an oxidizing agent such as hydrogen peroxide, tert-butyl hydroperoxide or peracetic acid may, if desired, be caused to act on it prior to, or during, the acid-cleavage reaction to convert 2-hydroxy-2-propyl-α,α-dimethylbenzyl hydroperoxide in the oxidation reaction product to m-DHP so that the yield of resorcinol will be increased.

As is well known, acid cleavage can be performed at a temperature of about 20° to about 120° C. in the presence of an acid catalyst such as sulfuric acid, perchloric acid, phosphoric acid, ion exchange resins, clays or synthetic silica alumina.

The acid-cleavage product contains phenols such as m-isopropylphenol and m-isopropenylphenol, ketones such as m-isopropenylacetophenone and carbinols such as m-isopropylcumyl alcohol in addition to acetone and resorcinol, although the types of these by-products differ depending upon the material to be acid-cleaved. It also contains high-boiling by-products which are presumably a condensate between resorcinol and acetone or condensates between resorcinol and olefins such as m-isopropenylphenol.

In the process of recovering resorcinol by thermally cracking high-boiling by-products contained in the acid-cleavage product of m-DHP which is formed by known means, the invention comprises effecting the thermal cracking in the presence of the aromatic ketone of formula (1).

These high-boiling by-products may be those containing resorcinol and low-boiling by-products (by-products having lower boiling points than resorcinol) which remain after removal of toluene and acetone from the acid-cleavage product of m-DHP, those containing resorcinol remaining after removal of a greater portion of the low-boiling by-products, or those substantially free from toluene, acetone, the low-boiling by-products and resorcinol. The removal can be performed by known methods such as distillation or extraction. When the removal is performed by distillation, high-boiling by-products will form. According to this invention, such additional high-boiling by-products formed in the distillation step can also be advantageously cracked.

Preferred high-boiling by-products to be cracked by the method of this invention are those containing up to about 60% by weight, based on the starting material to be cracked, of resorcinol and low-boiling by-products which remain after the removal of the acid catalyst from the acid-cleavage product by neutralization or filtration, and preferably after further removal of acetone and low-boiling substances such as the solvent used in the acid-cleavage reaction; or those containing more than 60% by weight, especially more than 70%, based on the material to be cracked, of high-boiling by-products and not more than 40% by weight, especially not more than 30% by weight, of low-boiling by-products and resorcinol which remain after further removal of a greater portion of the low-boiling by-products and resorcinol.

The thermal cracking in accordance with this invention can be performed in the presence or absence of a catalyst. The catalyst may, for example, be sulfuric acid and activated terra alba which are known catalysts. Investigations of the present inventors have shown that a metal selected from tin and zinc or its oxide can also be used as the catalyst. Compounds of such metals capable of being converted to the corresponding metals or metal oxides may be used. An especially preferred catalyst is metallic tin, and next comes metallic zinc or tin oxide. The form of the catalyst is optional, and it is generally used in the form of a powder, granules or a plate. Depending upon the reaction temperatures, the metallic tin is used in liquid form. The amount of the catalyst is not particularly restricted. Usually, the suitable amount is 0.01 to 5 parts by weight per 100 parts by weight of the material to be thermally cracked, although it may vary depending upon whether the thermal cracking is performed batchwise or continuously.

As stated hereinabove, the thermal cracking of high-boiling by-products is carried out in the presence of the aromatic ketone of formula (1).

Specific examples of the aromatic ketone are acetophenone, phenyl ethyl ketone, phenyl propyl ketone, phenyl butyl ketone, phenyl cyclohexyl ketone, benzophenone, tolymethyl ketone, m- and p-isopropyl acetophenones, m- and p-hydroxyacetophenones, o- and p-hydroxybenzophenones, diacetyl benzene, and o- and p-chloroacetophenones. These aromatic ketones may be used singly or as a mixture of two or more. Especially preferred aromatic ketones are m- and p-hydroxyacetophenones.

The amount of the aromatic ketone of formula (1) is preferably at least 7 parts by weight, more preferably at least 12 parts by weight, especially preferably at least 14 parts by weight, per 100 parts by weight of the high-boiling by-products. The use of a large amount of the aromatic ketone does not cause any appreciable trouble, but usually, it is used in an amount of up to 150 parts by weight per 100 parts by weight of the high-boiling by-products.

In the present invention, the aromatic ketone may be added to the cracking by-product system at the time of cracking. If desired, it may be caused to be present in the step of oxidizing m-DIPB, or in the step of acid cleaving m-DHP.

The temperature (the tower bottom temperature) of the thermal cracking is preferably about 170° to about 400° C., more preferably about 200° to about 330° C. The reaction time, which varies according to the thermal cracking temperature, is suitably about 0.1 to about 10 hours. When the thermal cracking temperature is too low, the rate of thermal cracking is too slow, and the process is inefficient. On the other hand, the use of excessively high thermal cracking temperature tends to induce coking, and will undesirably cause the clogging of the apparatus and accessory devices.

The mode of thermal cracking can be selected as required. For example, it is possible to perform the thermal cracking by using a thermal cracking reactor of the closed type, and isolating resorcinol, etc. from the thermally cracked product by extraction, distillation, etc. Preferably, however, resorcinol and other distillable components formed by the thermal cracking should be distilled out of the system rapidly so as to prevent their consumption by secondary reactions. For example, there can be employed a method in which the starting high-boiling by-products are continuously or batchwise fed into a thermal cracking apparatus and thermally cracked, and resorcinol and other distillable components are recovered by distillation at a pressure of about 5 to 70 mm Hg; and a method to which superheated steam or an inert gas is blown from the bottom of the distillation tower, and resorcinol, etc. is recovered from the tower top while entraining them by this gas.

The aromatic ketone used in the thermal cracking can be recovered for reuse by conventional means such as extraction or distillation.

The following examples illustrate the present invention more specifically.

EXAMPLES 1 TO 11 AND COMPARATIVE EXAMPLES 1 TO 4

From the reaction mixture obtained by the acid cleavage of the product of oxidation of m-DIPB, the solvent, resorcinol and by-products having lower boiling points than resorcinol were removed by distillation to separate resinous high-boiling by-products. Each of the aromatic ketones shown in Table 1 in the amounts indicated was added to 100 g of the high-boiling by-products, and the viscosity of the mixture was measured by using a Bismetron viscometer. The results are shown in Table 1.

Table 1

| Example | Aromatic ketone Type | Amount (g) | Measuring temperature (°C.) | Viscosity (centipoises) |
| --- | --- | --- | --- | --- |
| 1 | m-Hydroxyacetophenone | 5 | 250 | 4900 |
| 2 | " | 10 | " | 1050 |
| 3 | " | 15 | " | 660 |
| 4 | " | 25 | " | 135 |
| 5 | " | 5 | 300 | 2700 |
| 6 | " | 15 | " | 550 |
| 7 | p-Hydroxyacetophenone | " | 250 | 690 |
| 8 | " | 5 | 300 | 3200 |
| 9 | p-Chloroacetophenone | 15 | 250 | 725 |
| 10 | m-Tolyl methyl ketone | " | " | 900 |
| 11 | Benzophenone | 20 | " | 920 |
| Comp. Ex. | | | | |
| 1 | None | — | 250 | 16000 |
| 2 | " | — | 300 | 6400 |
| 3 | β-methylnaphthalene | 40 | 250 | 11000 |
| 4 | β-chloronaphthalene | 30 | " | 9200 |

EXAMPLE 12

The product of oxidation of m-DIPB was acid-cleaved in a toluene/acetone mixed solvent, and from the reaction mixture, toluene and acetone were distilled off to afford a composition (A) of the following composition.

| Low-boiling by-products | 22.5% by weight |
| --- | --- |
| Resorcinol | 33.6% by weight |
| High-boiling by-products | 43.9% by weight |

A preheater having an inside diameter of 5 mm and a length of 400 mm was mounted onto the third tray from the bottom of a 10-sieve tray distillation tower having an inside diameter of 35 mm with a distance between adjacent trays being 30 mm. To the composition (A) was added m-hydroxyacetophenone in an amount of 14% by weight based on the high-boiling by-products. The pre-heated was maintained at 280° C. and the bottom of the tower was heated to 290° C. The starting material prepared was then thermally cracked under a pressure of 8 to 14 mmHg while adjusting the rate of feeding the starting material to 320 ml/hr. During the distillation, the low-boiling by-products, resorcinol and 30%, based on the amount initially fed, of m-hydroxyacetophenone were continuously withdrawn from the top of the tower, and tarry components and 70%, based on the amount initially fed, of m-hydroxyacetophenone were withdrawn continuously from the bottom of the tower. After the thermal cracking was continued for 50 hours, there was hardly any adhesion of insoluble matter to the inner walls of the preheater and to the withdrawn line from the bottom of the tower.

EXAMPLE 13

The composition (A) of Example 12 was heated to 220° C., and distilled at 4 mmHg to afford composition (B) of the following composition.

| Low-boiling by-products | 2.0% by weight |
| --- | --- |
| Resorcinol | 11.5% by weight |
| High-boiling by-products | 86.5% by weight |

To the composition (B) was added m-hydroxyacetophenone in an amount of 14% by weight based on the high-boiling by-products. The resulting starting material was thermally cracked in the same apparatus as used in Example 12 for 50 hours. There was hardly any adhesion of insoluble matter to the inner walls of the preheater and to the withdrawing line from the bottom of the tower.

COMPARATIVE EXAMPLE 5

The procedure of Example 12 was repeated except that 30% by weight, based on the high-boiling by-products, of β-chloronaphthalene was used instead of the m-hydroxyacetophenone. After a lapse of 9 hours, insoluble matter adhered to the walls of the preheater and to the withdrawing line from the bottom of the tower. Thus, the thermal cracking could not be continued further.

What we claim is:

1. A method for recovering resorcinol by thermally cracking high-boiling by-products contained in the acid-cleavage product of m-diisopropylbenzene dihydroperoxide at a temperature of about 170° to about 400° C., wherein the thermal cracking is effected in the presence of at least 7 parts by weight, per 100 parts by weight of the high-boiling by-products, of an aromatic ketone of the formula

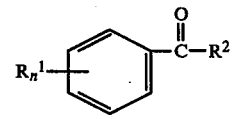

wherein $R^1$ represents a member selected from the group consisting of hydrogen, saturated alkyl groups having 1 to 6 carbon atoms, hydroxyl, acetyl and chlorine, $R^2$ represents a member selected from the group consisting of saturated alkyl groups having 1 to 6 carbon atoms, cyclohexyl and phenyl, and n represents 1, 2 or 3, and when there are two or more $R^1$ groups, they are identical or different.

2. The method of claim 1 wherein the amount of the aromatic ketone is at least 12 parts by weight per 100 parts by weight of the high-boiling by-products.

3. The method of claim 1 wherein the aromatic ketone is a member selected from the group consisting of acetophenone, phenyl ethyl ketone, phenyl propyl ketone, phenyl butyl ketone, phenyl cyclohexyl ketone, benzophenone, tolyl methyl ketone, isopropyl acetophenone, hydroxybenzophenone, diacetyl benzene, chloroacetophenone and mixtures of at least two of these.

4. The method of claim 1 wherein the aromatic ketone is m-hydroxyacetophenone, p-hydroxyacetophenone, or a mixture of both.

* * * * *